15

US011925312B2

(12) United States Patent
Uchida et al.

(10) Patent No.: US 11,925,312 B2
(45) Date of Patent: Mar. 12, 2024

(54) ENDOSCOPE

(71) Applicant: OLYMPUS CORPORATION, Tokyo (JP)

(72) Inventors: Ramiya Uchida, Tachikawa (JP); Masanobu Koitabashi, Hachioji (JP); Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 439 days.

(21) Appl. No.: 17/348,374

(22) Filed: Jun. 15, 2021

(65) Prior Publication Data

US 2021/0345858 A1 Nov. 11, 2021

Related U.S. Application Data

(63) Continuation of application No. PCT/JP2019/000095, filed on Jan. 7, 2019.

(51) Int. Cl.
*A61B 1/00* (2006.01)
*A61B 1/005* (2006.01)

(52) U.S. Cl.
CPC ...... *A61B 1/00027* (2013.01); *A61B 1/00018* (2013.01); *A61B 1/00101* (2013.01);
(Continued)

(58) Field of Classification Search
CPC .......................... A61B 1/00027; A61B 1/00018
See application file for complete search history.

(56) References Cited

U.S. PATENT DOCUMENTS 6,793,622 B2 * 9/2004 Konomura ......... G02B 23/2476
600/152
9,265,405 B2 * 2/2016 Okamoto ........... A61B 1/00148
(Continued)

FOREIGN PATENT DOCUMENTS

JP  H11-32977 A   2/1999
JP  2001-087220 A  4/2001
(Continued)

OTHER PUBLICATIONS

International Search Report dated Mar. 12, 2019 received in PCT/JP2019/000095.

*Primary Examiner* — John P Leubecker
*Assistant Examiner* — Jae Woo
(74) *Attorney, Agent, or Firm* — Scully, Scott, Murphy & Presser, P.C.

(57) ABSTRACT

An endoscope includes an insertion portion, an operation portion, a power transmission unit, a power relay unit, a power generation unit configured to apply power to the power relay unit in a second power transmission shaft direction which is non-parallel to a first power transmission shaft direction, an elastic member configured to perform either one of urging the power relay unit against the power generation unit or urging the power generation unit against the power relay unit, and a cable configured to extend from the operation portion in the second power transmission shaft direction which is a direction different from a longitudinal direction, wherein the power generation device is attached such that the power generation device is disposed to extend in an extending direction of the cable after being mounted.

11 Claims, 12 Drawing Sheets

(52) U.S. Cl.
CPC ............ *A61B 1/005* (2013.01); *A61B 1/0052* (2013.01); *A61B 2560/0214* (2013.01)

(56) References Cited

U.S. PATENT DOCUMENTS

| | | | |
|---|---|---|---|
| 10,835,108 B2* | 11/2020 | Sholev | A61B 1/0016 |
| 2013/0060088 A1* | 3/2013 | Okamoto | A61B 1/0052 600/146 |
| 2014/0180008 A1* | 6/2014 | Okamoto | A61B 1/0052 600/132 |
| 2016/0331210 A1* | 11/2016 | Onoda | A61B 1/00006 |
| 2019/0110666 A1* | 4/2019 | Masaki | A61B 1/0016 |

FOREIGN PATENT DOCUMENTS

| | | |
|---|---|---|
| JP | 3222190 B2 | 10/2001 |
| JP | 2005-279119 A | 10/2005 |
| JP | 2005279119 A * | 10/2005 |
| JP | 2005-349180 A | 12/2005 |
| WO | 2006/059722 A1 | 6/2006 |
| WO | 2012/117865 A1 | 9/2012 |

\* cited by examiner

ENDOSCOPE

CROSS REFERENCE TO RELATED APPLICATION

This application is a continuation application of PCT/JP2019/000095 filed on Jan. 7, 2019, the entire contents of which are incorporated herein by this reference.

BACKGROUND OF THE INVENTION

1. Field of the Invention

The present invention relates to an endoscope to which a power generation unit is attached, the power generation unit applying power to a specific portion of an insertion portion.

2. Description of the Related Art

In recent years, endoscopes have been widely used in a medical field and an industrial field. By inserting an elongated insertion portion into an object or a subject, the endoscope can perform, for example, observation or treatment of a site to be examined in the object or the subject.

Further, there is a well-known configuration where a specific portion, for example, a bending portion which is bendable in a plurality of directions, is provided on a distal end side of an insertion portion of an endoscope in a longitudinal direction (hereinafter simply referred to as "distal end side").

The bending portion increases ease of progressing of the insertion portion through a bent portion of a conduit, and changes an observation direction of an observation optical system provided to a distal end portion of the insertion portion, the distal end portion being located at a position closer to the distal end side than the bending portion.

The bending portion is configured to be bendable in any one of four directions, being an upward direction, a downward direction, a leftward direction, or a rightward direction, for example, with a rotating operation of a knob performed by an operator, the knob being provided to an operation portion of the endoscope to protrude toward one side in a direction intersecting with the above-mentioned longitudinal direction.

Specifically, the bending portion is configured such that, when the knob is rotated, a power transmission unit is activated, so that the bending portion is bent.

More specifically, the bending portion is configured such that, with the rotation of a pulley which rotates together with the knob provided in the operation portion, a long member, such as a chain or a wire, is pulled, so that the bending portion is bent, the long member being wound around the pulley, and a distal end of the long member in the longitudinal direction (hereinafter, simply referred to as "distal end") being fixed to the bending portion.

The rotating operation of the knob is performed by a thumb of a left hand in a state where a grasping area of the operation portion is grasped by a palm, a little finger, a ring finger, and a middle finger of a left hand of the operator, and a fixed portion side of a universal cord extending from the operation portion is grasped such that the fixed portion side is sandwiched between the forefinger and the thumb of the left hand.

When the insertion portion of the endoscope is inserted into the object or the subject, the operator grasps the insertion portion with a right hand to perform pushing operation of the insertion portion into deep parts of the object or the subject with the right hand, and the operator grasps the operation portion as described above with the left hand to perform an operation of the above-mentioned knob or various switches provided to the operation portion.

However, there is a problem that, due to a large amount of operation, it is difficult for an operator with small hands or an operator who is unfamiliar with the endoscope to perform the rotating operation of the knob with the thumb of the left hand as described above to pull the long member.

In view of such a problem, Japanese Patent No. 3222190 discloses a configuration where a rotating operation of a knob is performed by an electric mechanism with a switching operation so as to reduce the amount of rotating operation of the knob.

Specifically, Japanese Patent No. 3222190 discloses the configuration of a power transmitting mechanism where an outer periphery of the knob is covered by a wheel, and the wheel is electrically rotated by a power generation unit, which is mounted on an operation portion, with the switching operation performed by an operator, so that the rotation of the knob is performed by an electric mechanism.

SUMMARY OF THE INVENTION

An aspect of the present invention is directed to an endoscope including: an insertion portion configured to be inserted into an object or a subject; an operation portion provided on a proximal end side of the insertion portion in a longitudinal direction in which the insertion portion extends, the operation portion being grasped by an operator, and being configured to perform an operation of the insertion portion; a power transmitting mechanism provided in the operation portion, and configured to transmit power to a specific portion of the insertion portion; a power relay mechanism connected to the power transmitting mechanism, and configured to transmit the power to the power transmitting mechanism; a power generation device attached adjacent to the power relay mechanism, and configured to apply the power to the power relay mechanism in a second power transmission shaft direction which is non-parallel to a first power transmission shaft direction of the power transmitting mechanism; an elastic member configured to perform either one of urging the power relay mechanism against the power generation mechanism or urging the power generation device against the power relay mechanism; and a cable configured to extend from the operation portion in the second power transmission shaft direction which is a direction different from the longitudinal direction, wherein the power generation device is attached such that the power generation device is disposed to extend in an extending direction of the cable after being mounted.

DETAILED DESCRIPTION OF THE PREFERRED EMBODIMENTS

Hereinafter, embodiments of the present invention will be described with reference to drawings.

First Embodiment

Figure 1:
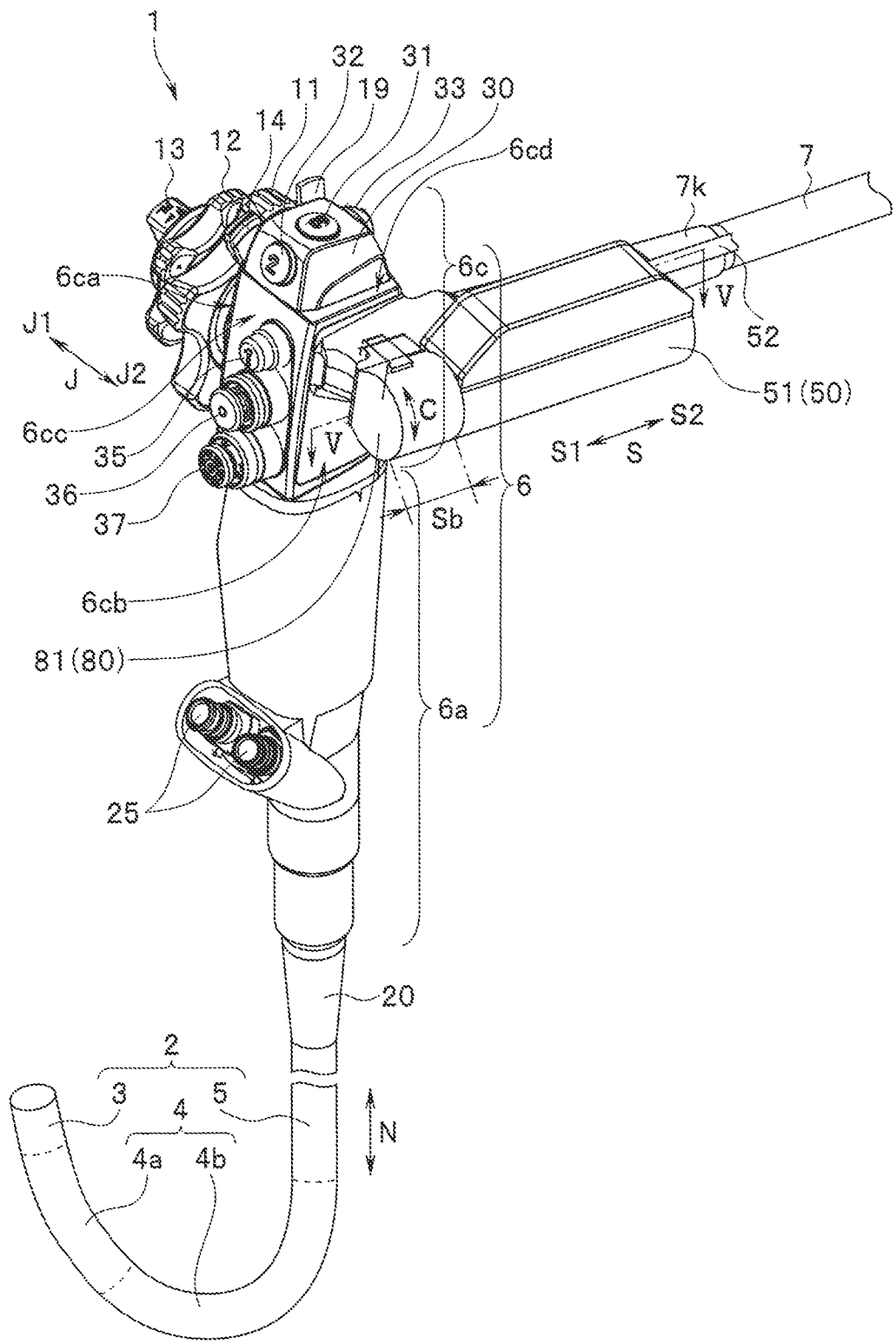
FIG. 1 is a partial perspective view showing an endoscope of a first embodiment.
Figure 2:
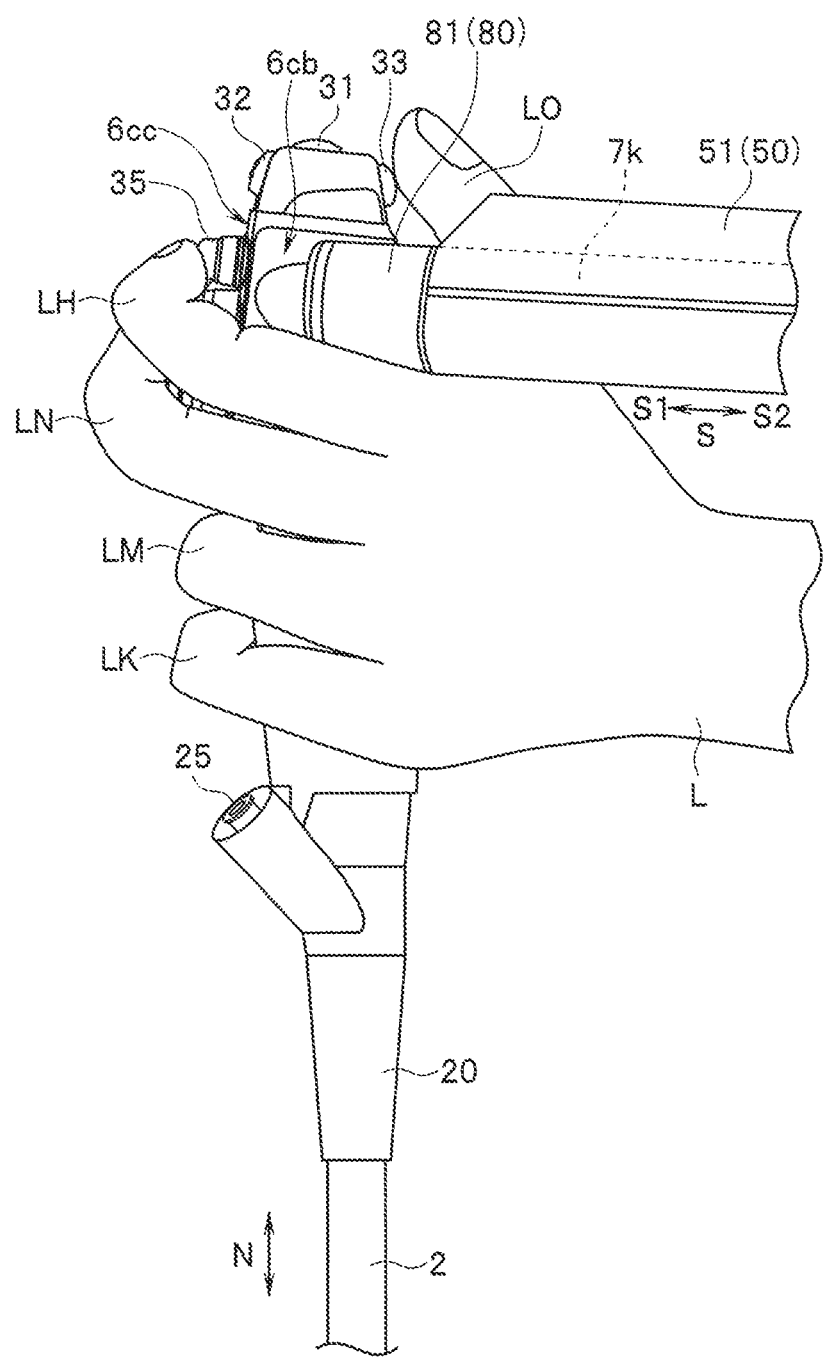
FIG. 2 is a view showing a state where an operation portion of the endoscope shown in FIG. 1 is grasped by a left hand of an operator.

FIG. 1 is a partial perspective view showing an endoscope of the present embodiment. FIG. 2 is a view showing a state where an operation portion of the endoscope shown in FIG. 1 is grasped by a left hand of an operator.

As shown in FIG. 1, an endoscope 1 includes an insertion portion 2 and an operation portion 6. The insertion portion 2 is inserted into an object or a subject. The operation portion 6 is provided on the proximal end side of the insertion portion 2 in a longitudinal direction N (hereinafter simply referred to as "proximal end side"), and is grasped and operated by the operator.

The endoscope 1 also includes a universal cord 7 and a connector not shown in the drawing. The universal cord 7 is a cable extending from the operation portion 6. The connector is provided to an extension end of the universal cord 7.

The connector is connectable to a known light source device, a known video processor, or the like not shown in the drawing and hence, the endoscope 1 is connectable to a peripheral device.

A main part of the insertion portion 2 is formed by including, in order from the distal end side, a distal end portion 3, a bending portion 4, and a flexible tube portion 5. The distal end portion 3 includes an image pickup unit not shown in the drawing.

In the present embodiment, the bending portion 4 includes a first bending portion 4a and a second bending portion 4b. The first bending portion 4a is the other specific portion located on the distal end side. The second bending portion 4b is a specific portion which is continuously formed with the proximal end of the first bending portion 4a in the longitudinal direction N (hereinafter simply referred to as "proximal end").

The bending portion 4 may include only the first bending portion 4a.

However, hereinafter, the description will be made by taking a case where the bending portion 4 includes the first bending portion 4a and the second bending portion 4b, as an example.

The operation portion 6 includes, in order from the distal end side, a grasping area 6a and an operation element area 6c which is continuously formed with the proximal end of the grasping area 6a. The operation portion 6 is continuously formed with the proximal end of the flexible tube portion 5 via a known bend preventing portion 20.

As shown in FIG. 2, the grasping area 6a is an area (grasping portion) which is grasped by a palm, a middle finger LN, a ring finger LM, and a little finger LK of a left hand L of the operator.

The grasping area 6a has treatment instrument insertion openings 25 on the distal end side. The treatment instrument insertion openings 25 are provided to allow a treatment instrument not shown in the drawing to be inserted into and removed from a treatment instrument insertion passage not shown in the drawing which is provided in the operation portion 6 and the insertion portion 2.

Note that, in FIG. 1, two treatment instrument insertion openings 25 are provided. However, one treatment instrument insertion opening 25 may be provided as a matter of course.

The operation element area 6c is provided with various operation elements which are operated by the operator, such as bending operation knobs 11, 12, a fixing knob 13, a fixing lever 14, and an electric bending operation lever 19.

With the rotating operation of the bending operation knobs 11, 12 which is performed by a thumb LO of the left hand L of the operator, for example, the bending operation knobs 11, 12 cause the bending operation of the first bending portion 4a in four directions, being an upward direction, a downward direction, a leftward direction or a rightward direction, for example, via a known power transmission unit not shown in the drawing, which is provided in the insertion portion 2 and the operation portion 6.

With the rotating operation of the fixing knob 13 which is performed by the thumb LO, for example, the fixing knob 13 fixes the rotational position of the bending operation knob 12. With the rotating operation of the fixing lever 14 which is performed by the thumb LO, for example, the fixing lever 14 fixes the rotational position of the bending operation knob 11.

With the rotating operation of the electric bending operation lever 19 which is performed by the thumb LO, for example, the electric bending operation lever 19 causes a power generation unit 50 (see FIG. 2) to be driven so as to transmit power of the power generation unit 50 to a power transmission unit 40 (see FIG. 4) via a power relay unit 80 (see FIG. 2). The power generation unit 50 is a power generation device, which will be described later. The power relay unit 80 is a power relay mechanism, which will be described later. The power transmission unit 40 is a power transmitting mechanism, which will be described later. With such a configuration, the electric bending operation lever 19 causes the bending operation of the second bending portion 4b in at least one direction.

Therefore, the bending action of the first bending portion 4a, which is performed by the bending operation knobs 11, 12, differs from the bending action of the second bending portion 4b, in which power is transmitted from the power generation unit 50 via the power relay unit 80 and the power transmission unit 40, the bending action of the second bending portion 4b being performed by the electric bending operation lever 19.

Note that the bending operation of the second bending portion 4b is not limited to be performed by the above-mentioned electric bending operation lever 19, but may be performed by any element, such as a knob or a switch button provided to the operation portion 6, or a foot switch connected to the endoscope 1 or to the peripheral device connected to the endoscope 1, as long as the element can command the power generation unit 50 to drive.

In contrast to the above, the bending operation of the second bending portion 4b may be performed by using the bending operation knobs 11, 12, or the bending operation of the first bending portion 4a may be performed by using the electric bending operation lever 19.

As shown in FIG. 1, the bending operation knobs 11, 12, the fixing knob 13, the fixing lever 14, and the electric bending operation lever 19 are provided to protrude toward a first side J1 of a direction J, intersecting with the longitudinal direction N, from a surface 6ca of the outer surface of the operation element area 6c, the first side J1 being a side directing away from the surface 6ca in the direction J.

A freeze switch button 35, a suction operation switch button 36, and an air/water feeding operation switch button 37, for example, are provided to a surface of the outer surface of the operation element area 6c which is disposed adjacent to the surface 6ca, specifically, to a surface 6cc on the same direction side as the surface having the treatment instrument insertion openings 25 as shown in FIG. 1. The freeze switch button 35 commands an image being picked up by the image pickup unit to pause.

In the case where the operation portion 6 is grasped by the operator as shown in FIG. 2, the freeze switch button 35, the suction operation switch button 36, and the air/water feeding operation switch button 37 are operated by a forefinger LH or the middle finger LN.

Needless to say, the above-mentioned functions of the switch buttons 35 to 37 are merely examples, and are not limited to the above-mentioned functions.

Further, a switch box 30 is provided to a surface 6cd of the outer surface of the operation element area 6c. The surface 6cd is disposed adjacent to the surface 6ca and the surface 6cc, and is disposed on the far side which is farther separated from the insertion portion 2 in the longitudinal direction N than a position where the above-mentioned switch buttons 35 to 37 are provided.

The top portion of the switch box 30 in the longitudinal direction N is provided with a power supply switch button 31 that turns on and off the power source of the endoscope 1, for example.

An iris switch button 32 is provided to the surface of the switch box 30 which is disposed on the same side as the surface to which the switch buttons 35 to 37 are provided. The iris switch button 32 changes a photometry method, for example.

A release switch button 33 is further provided to the surface of the switch box 30 on the side opposite to the iris switch button 32. The release switch button 33 commands recording of an image being picked up by the image pickup unit, for example.

Note that in the case where the operation portion 6 is grasped as shown in FIG. 2, the switch button 33 is operated by the thumb LO of the left hand L, for example.

In the case where the operation portion 6 is grasped as shown in FIG. 2, the switch buttons 31, 32 are operated by the forefinger LH of the left hand L, for example. The switch button 32 may be operated by the thumb LO.

Needless to say, the above-mentioned functions of the switch buttons 31 to 33 are merely examples, and are not limited to the above-mentioned functions.

A surface 6cb of the outer surface of the operation element area 6c is disposed adjacent to the surface 6cc and the surface 6cd, and is disposed on a side opposite to the surface 6ca in the direction J. On the surface 6cb, a bend preventing portion 7k of the universal cord 7 is fixed to a frame 120, which will be described later (see FIG. 3), such that the bend preventing portion 7k protrudes toward a second side J2 of the direction J, which is a side opposite to the first side J1, the frame 120 being provided to protrude toward the second side J2 from the inside of the operation element area 6c.

With such a configuration, the universal cord 7 extends in a direction S substantially orthogonal to the direction J in a state where the end portion of the bend preventing portion 7k is fixed to the frame 120.

The power relay unit 80, forming a portion of the operation portion 6, is provided to an opposite side of the first side J1 in the direction J with respect to the operation element area 6c such that the power relay unit 80 protrudes toward the second side J2 from a position where the bend preventing portion 7k of the universal cord 7 is fixed to the surface 6cb.

To allow transmission of power, the power generation unit 50 is attached adjacent to the power relay unit 80. The power generation unit 50 may have a structure where the power generation unit 50 is detachable from and attachable to the power relay unit 80 via a cam mechanism or the like, which will be described later. When the power generation unit 50 is mounted on the power relay unit 80, as shown in FIG. 1, the power generation unit 50 is disposed to extend in the direction S, which is an extending direction of the universal cord 7.

Next, the detailed configuration of the power transmission unit 40, being a power transmitting mechanism, the power relay unit 80, and the power generation unit 50 will be described with reference to FIG. 3 to FIG. 9.

Figure 3:
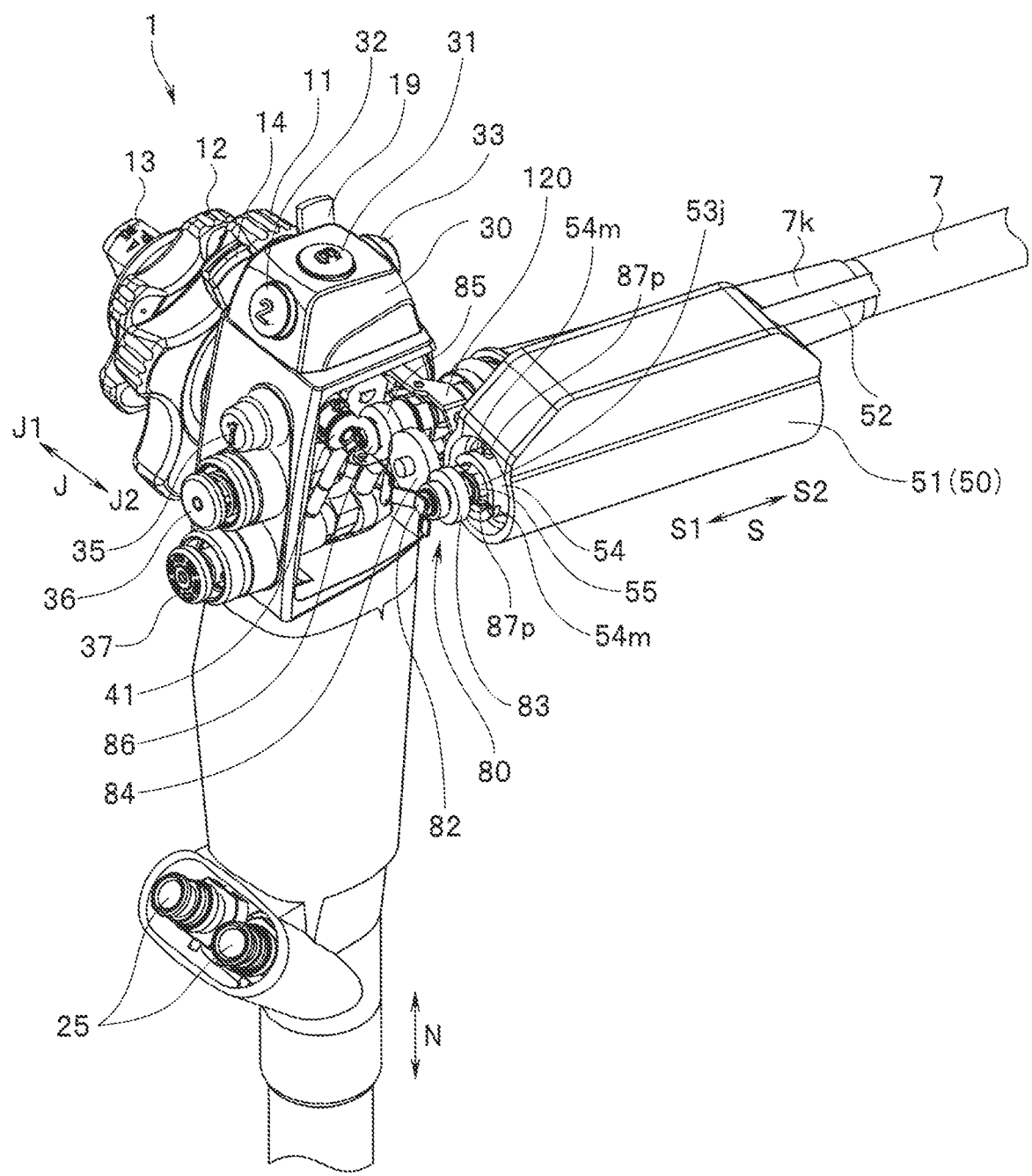
FIG. 3 is a partial perspective view showing a state where a second casing of a power relay unit and a portion of an exterior of an operation element area of the operation portion are removed from the endoscope shown in FIG. 1.
Figure 4:
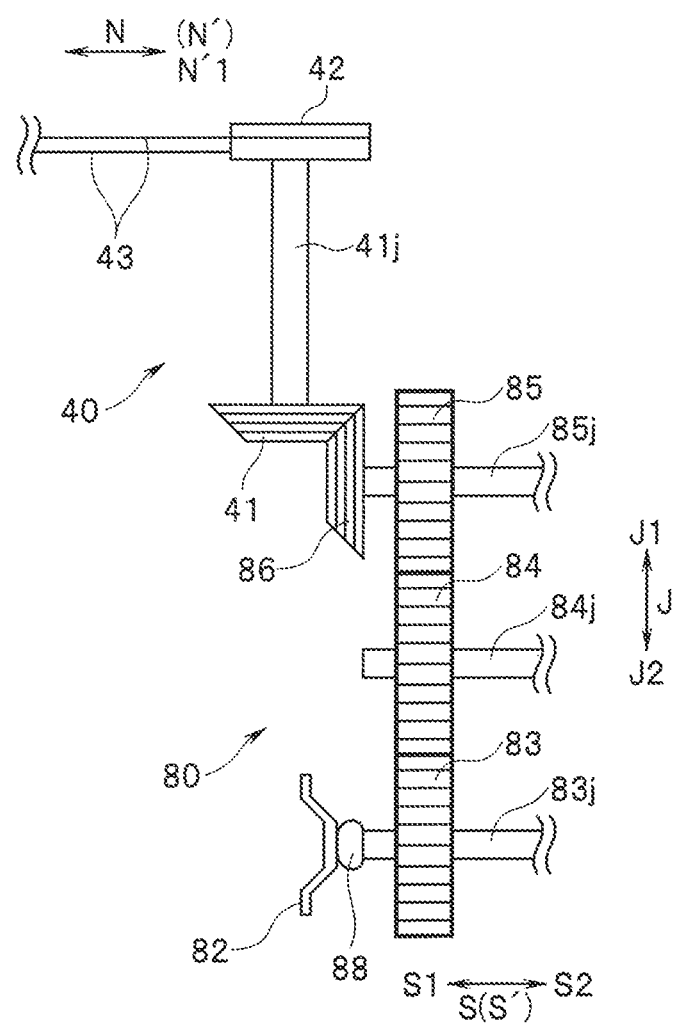
FIG. 4 is a view schematically showing a power transmission configuration of a power generation unit, the power relay unit, and a power transmission unit shown in FIG. 3.

FIG. 3 is a partial perspective view showing a state where a second casing of the power relay unit and a portion of the exterior of the operation element area of the operation portion are removed from the endoscope shown in FIG. 1. FIG. 4 is a view schematically showing the power transmission configuration of the power generation unit, the power relay unit, and the power transmission unit shown in FIG. 3.

Figure 5:
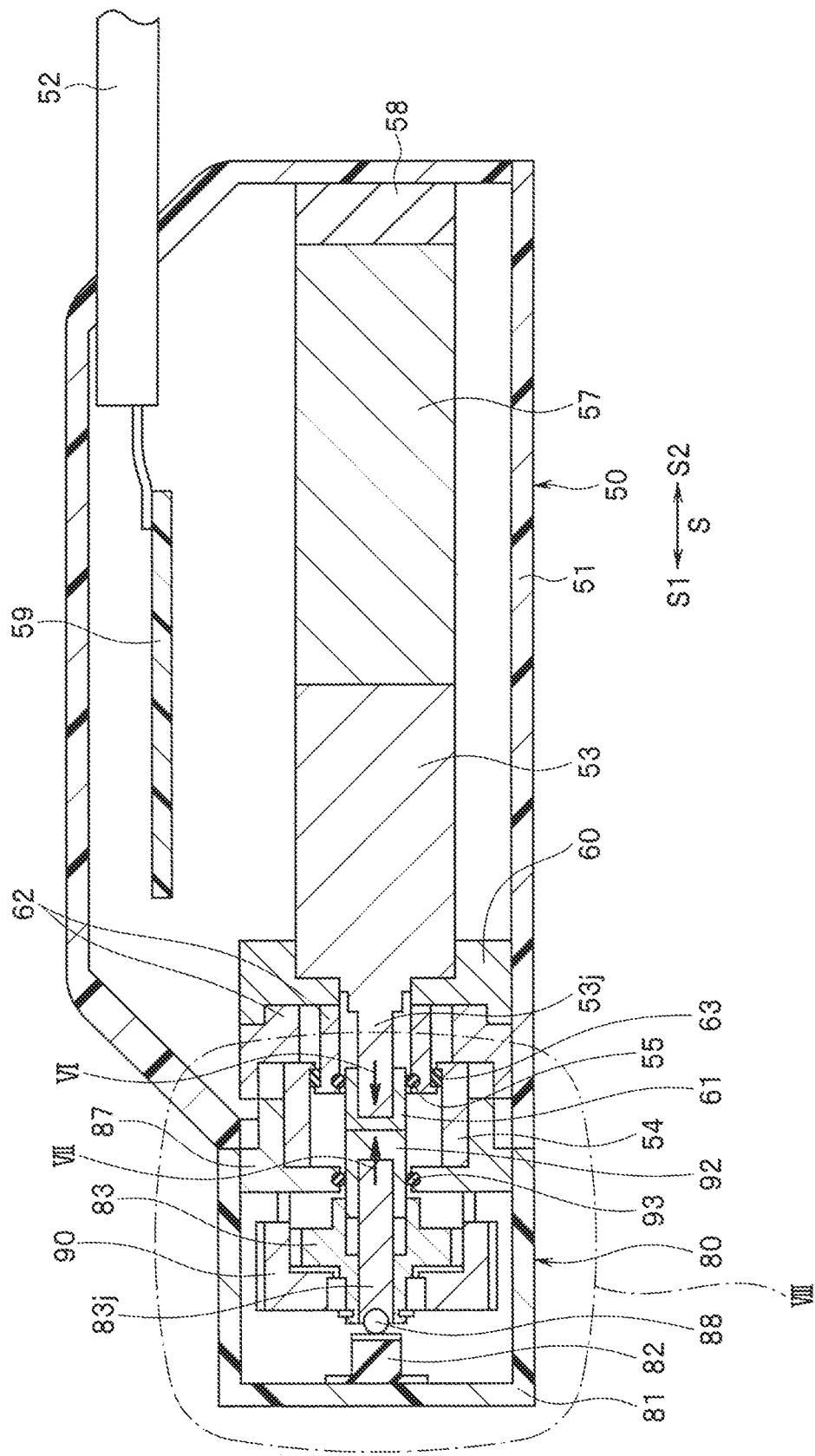
FIG. 5 is a cross-sectional view of the power relay unit and the power generation unit taken along line V-V in FIG. 1.
Figure 6:
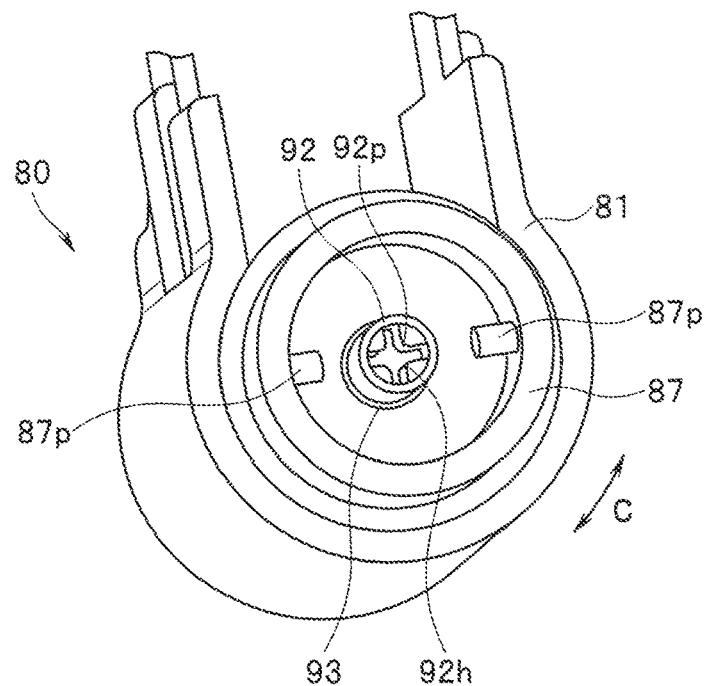
FIG. 6 is a perspective view of the second casing, a relay unit holding frame, and a relay unit rotation shaft of the power relay unit shown in FIG. 5 as viewed in a VI direction in FIG. 5.
Figure 7:
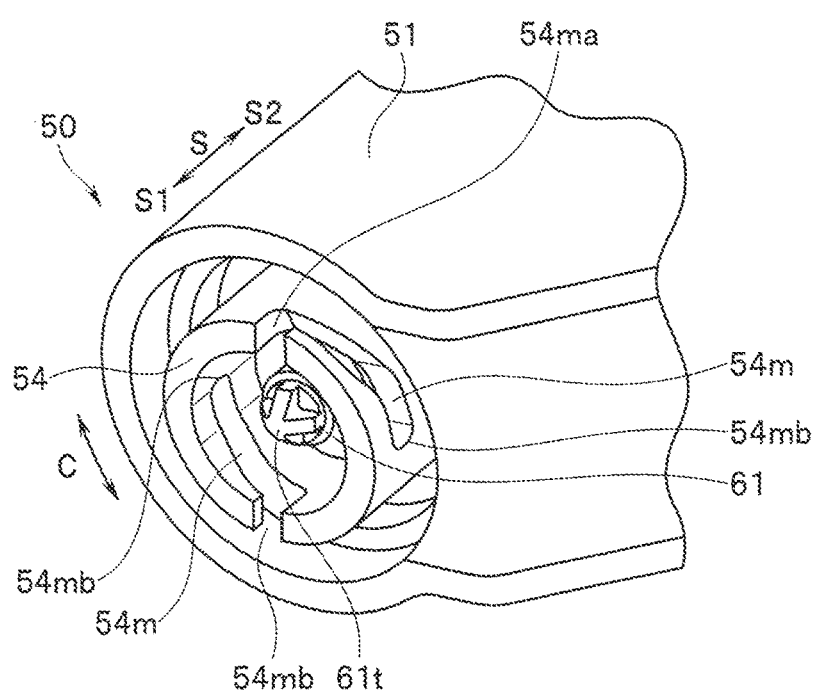
FIG. 7 is a perspective view of a first casing, a generation unit holding frame, and a generation unit rotation shaft of the power generation unit shown in FIG. 5 as viewed in a VII direction in FIG. 5.

FIG. 5 is a cross-sectional view of the power relay unit and the power generation unit taken along line V-V in FIG. 1. FIG. 6 is a perspective view of the second casing, a relay unit holding frame, and a relay unit rotation shaft of the power relay unit shown in FIG. 5 as viewed in a VI direction in FIG. 5. FIG. 7 is a perspective view of a first casing, a generation unit holding frame, and a generation unit rotation shaft of the power generation unit shown in FIG. 5 as viewed in a VII direction in FIG. 5.

Figure 8:
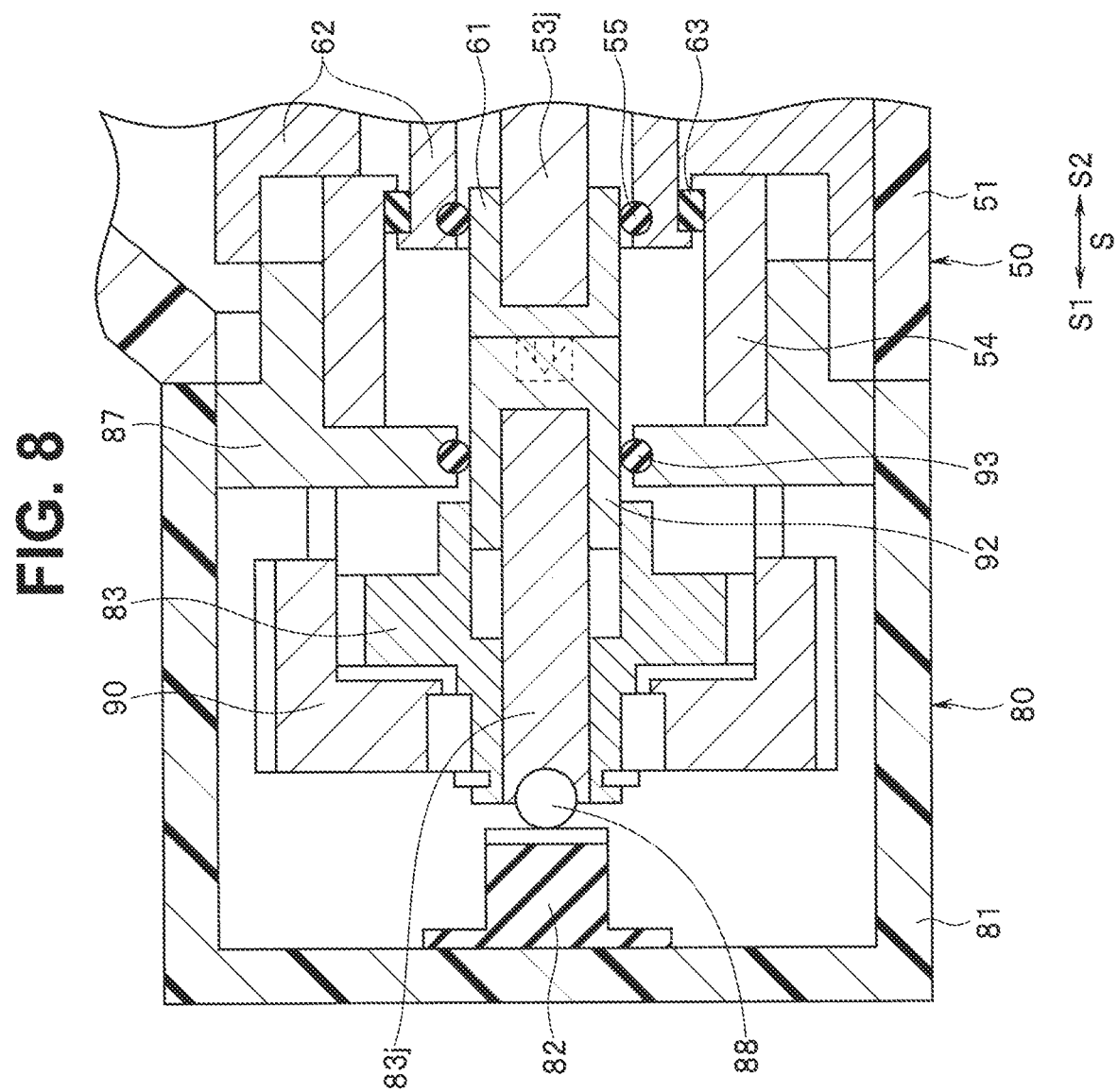
FIG. 8 is a cross-sectional view showing a portion surrounded by a line VIII in FIG. 5 in an enlarged manner.
Figure 9:
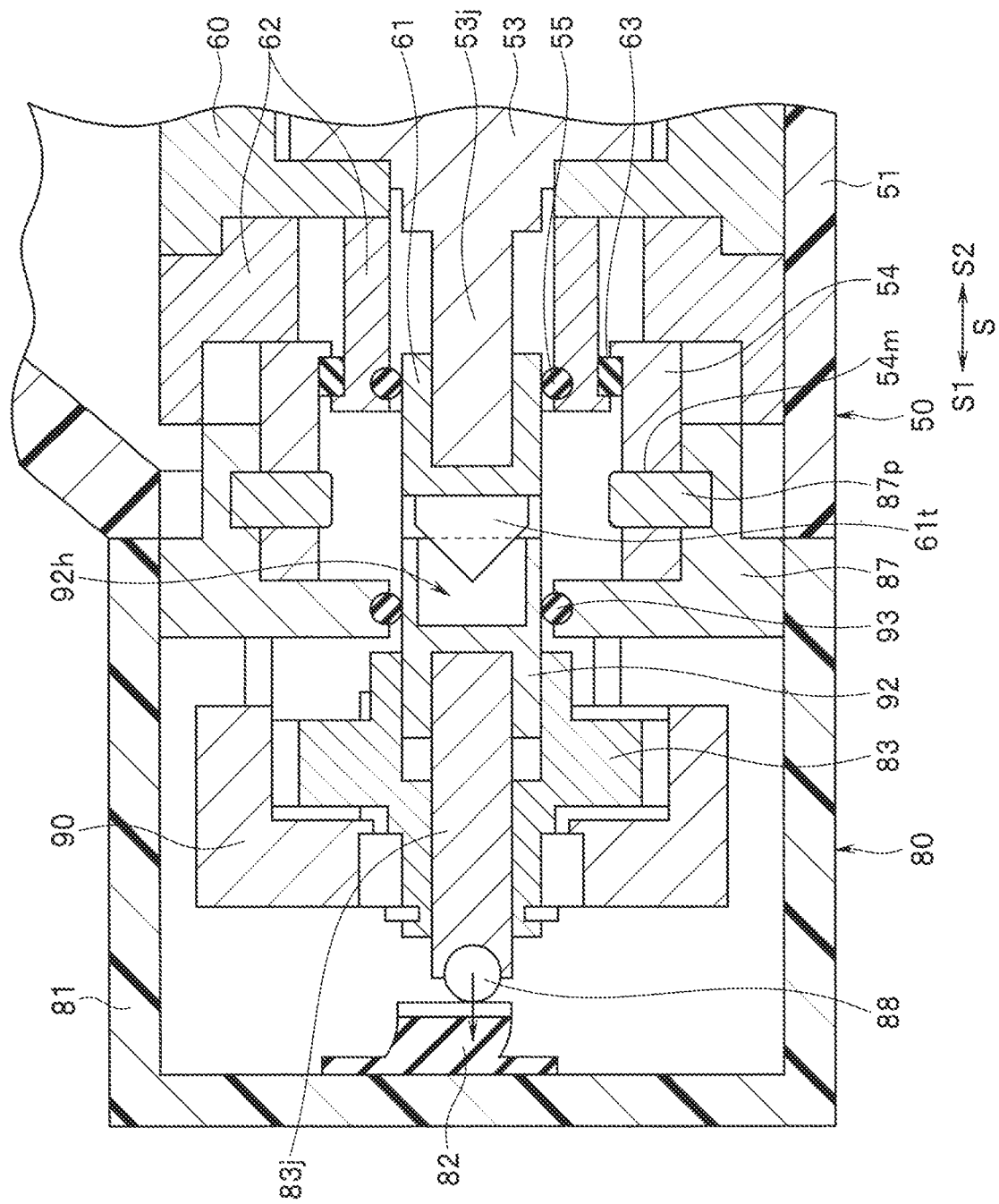
FIG. 9 is a cross-sectional view showing a state where an elastic member of the power relay unit is pushed when the power generation unit is mounted on the power relay unit shown in FIG. 8.

FIG. 8 is a cross-sectional view showing a portion surrounded by a line VIII in FIG. 5 in an enlarged manner FIG. 9 is a cross-sectional view showing a state where an elastic member of the power relay unit is pushed when the power generation unit is mounted on the power relay unit shown in FIG. 8.

The power transmission unit 40 is provided in the operation portion 6 and the insertion portion 2 to transmit power to the second bending portion 4b.

Specifically, as shown in FIG. 4, the main part of the power transmission unit 40 includes a pulley 42, two long members 43, a bevel gear 41, and a shaft 41*j*. The pulley 42 is provided in the operation element area 6*c* of the operation portion 6. The two long members 43 are wires or chains, for example, which are wound around the pulley 42, and are provided in the operation portion 6 and the insertion portion 2. Only one long member 43 may be provided.

The distal end of each of the two long members 43 in the longitudinal direction N is fixed to the distal end of the second bending portion 4*b*. Each of the two long members 43 can be moved in a first power transmission shaft direction N' which is substantially parallel to the longitudinal direction N.

Therefore, when the pulley 42 is rotated in one direction, one long member 43 is pulled toward a rear side Ni' in the first power transmission shaft direction N' and hence, the second bending portion 4*b* is bent in one direction.

When the pulley 42 is rotated in the other direction, the other long member 43 is pulled toward the rear side Ni' in the first power transmission shaft direction N' and hence, the second bending portion 4*b* is bent in the other direction.

The end portion of the shaft 41*j* on the first side J1 of the direction J is connected to the pulley 42, and the end portion of the shaft 41*j* on the second side J2 is connected to the bevel gear 41.

Therefore, when the bevel gear 41 rotates, the rotational force is transmitted to the pulley 42 via the shaft 41*j*. In other words, the pulley 42 is rotatable in one direction or the other direction with the rotation of the bevel gear 41.

The power relay unit 80, being the power relay mechanism, is connected to the power transmission unit 40 to transmit a rotational force, being power, to the power transmission unit 40.

Specifically, the main part of the power relay unit 80 is formed such that a second casing 81 houses an elastic member 82, a spur gear 83, a relay unit rotation shaft 83*j* which pivotally supports the spur gear 83, an idler gear 84, a shaft 84*j* which pivotally supports the idler gear 84, a spur gear 85, a bevel gear 86, a shaft 85*j* which pivotally supports the bevel gear 86 and the spur gear 85, a relay unit holding frame 87, and a gear box 90.

The bevel gear 86 is pivotally supported by the same shaft 85*j* as the spur gear 85, and is meshed with the bevel gear 41. With such a configuration, the bevel gear 86 has a function of transmitting a rotational force of the shaft 85*j* to the bevel gear 41.

As shown in FIG. 3, the shaft 85*j* is pivotally supported such that the shaft 85*j* can be rotated with respect to the frame 120, which is provided to protrude toward the second side J2 from the inside of the operation element area 6*c*, for example.

The spur gear 85 is meshed with the idler gear 84 pivotally supported by the shaft 84*j*. The shaft 84*j* is also pivotally supported such that the shaft 84*j* can be rotated with respect to the frame 120.

Therefore, the spur gear 85 has a function of rotating the shaft 85*j* with the transmission of the rotational force from the idler gear 84.

The idler gear 84 is disposed on the second side J2 of the spur gear 85 in the direction J, and is meshed with the spur gear 85 and the spur gear 83. The idler gear 84 transmits the rotational force of the spur gear 83 to the spur gear 85.

To reduce the size of the power relay unit 80 in the direction J, it may be possible to adopt a configuration where the idler gear 84 is not provided, and the spur gear 83 is directly meshed with the spur gear 85 to directly transmit a rotational force of the spur gear 83 to the spur gear 85.

As shown in FIG. 5, the spur gear 83 is provided in the gear box 90 in the second casing 81, and is meshed with the idler gear 84 in a state of being disposed on the second side J2 of the idler gear 84 in the direction J.

The spur gear 83 is pivotally supported on the relay unit rotation shaft 83*j* such that the spur gear 83 can be rotated, the relay unit rotation shaft 83*j* being positioned to extend in a second power transmission shaft direction S' which is substantially parallel to the direction S, and which is non-parallel to the first power transmission shaft direction N.

The spur gear 83 transmits the rotational force transmitted from the relay unit rotation shaft 83*j* to the idler gear 84.

In other words, as shown in FIG. 3 and FIG. 4, when the relay unit rotation shaft 83*j* is rotated, the spur gear 83 rotates, so that the rotational force is transmitted to the idler gear 84, the spur gear 85, and the shaft 85*j* in the direction J, thus rotating the bevel gear 86.

Thereafter, the bevel gear 41 which is meshed with the bevel gear 86 is rotated and hence, the rotation direction is changed, and the shaft 41*j* is rotated, thus rotating the pulley 42.

As a result, either one of the two long members 43 is pulled due to the rotation, so that the second bending portion 4*b* is bent in either one of two directions in the present embodiment.

If the respective gears 41, 86, 85, 84, 83 are made of a resin, there are advantageous effects that periodical oil injection to meshed portions can be eliminated and meshing sound generated with the rotation of the gears can be reduced.

As described above, the bevel gears are used for changing a direction in which a rotational force is transmitted. With such a configuration, it is also possible to obtain an advantageous effect that meshing sound generated with the rotation of the gears can be reduced.

Further, by setting the number of teeth of the respective gears, that is, the spur gear 85, the idler gear 84, and the spur gear 83, to different non-integers, it is possible to reduce the number of times that the same teeth are meshed with each other at the time of meshing and hence, wear on the teeth can be reduced.

For the transmission of a rotational force from the relay unit rotation shaft 83*j* to the shaft 85*j*, three spur gears which are arranged in the direction J, that is, the spur gear 85, the idler gear 84, and the spur gear 83, are used and hence, it is possible to reduce a rotation speed to an appropriate speed by these three spur gears.

In the present embodiment, a spur gear train including the three gears 83 to 85 is used to transmit the rotational force of the relay unit rotation shaft 83*j* to the shaft 85*j*. However, the configuration is not limited to the above, and a toothed belt, chains or the like may be used.

The end portion of the relay unit rotation shaft 83*j* on one side S1 in the direction S is provided with a ball 88 which can be brought into contact with the elastic member 82. A cap member 92 is fixed to the outer periphery of the end portion of the relay unit rotation shaft 83*j* on the other side S2 in the direction S in a state of covering the outer periphery of the end portion, the cap member 92 having a substantially angled-U shape in cross section.

As shown in FIG. 6, the end surface of the cap member 92 on the other side S2 has a recessed portion 92*h* which is recessed toward the one side S1.

The bottom surface of the recessed portion 92*h* has a cross-shaped recessed portion 92*p* having a cross shape as viewed in a plan view. The cross shape as viewed in a plan view of the recessed portion 92p merely forms an example, and the recessed portion 92p may have an elliptical shape as viewed in a plan view, for example.

The outer periphery of the cap member 92 is covered by the relay unit holding frame 87 via an O-ring 93 such that the relay unit holding frame 87 is coaxial with the relay unit rotation shaft 83j in the direction S.

Note that the relay unit holding frame 87 is fixed to the inner peripheral surface of the second casing 81. Therefore, there is no possibility that the relay unit holding frame 87 rotates in a circumferential direction C of the relay unit rotation shaft 83j with the rotation of the relay unit rotation shaft 83j.

The relay unit rotation shaft 83j and the cap member 92 can not only be rotated with respect to the relay unit holding frame 87 in the circumferential direction C but can also be moved with respect to the relay unit holding frame 87 toward the one side S1 and the other side S2 in the direction S in a state of being in contact with the O-ring 93.

The inner peripheral surface of the relay unit holding frame 87 has two cam protrusions 87p at positions which face the outer periphery of the cap member 92, the two cam protrusions 87p facing each other.

In attaching the power generation unit 50 to the power relay unit 80, as shown in FIG. 5 and FIG. 8, the power generation unit 50 is attached such that a cam cylinder 54, which will be described later, is fitted into the relay unit holding frame 87 in the direction S.

The elastic member 82 is formed of a leaf spring or a coil spring, for example. Further, the elastic member 82 is fixed in the second casing 81 by welding, screws, adhesion or the like such that the elastic member 82 faces the ball 88.

With the urging of the ball 88 toward the other side S2 in the direction S, the elastic member 82 causes the power relay unit 80 to be brought into close connect with the power generation unit 50 to apply the rotational force of the power generation unit 50 to the power relay unit 80 with certainty. The manner of operation of the elastic member 82 will be described later in detail.

The power generation unit 50, being the power generation device, applies power to the power relay unit 80 in the direction S. Specifically, the main part of the power generation unit 50 is formed such that a first casing 51 houses the end portion of a cable 52, a gear head 53, the cam cylinder 54, being a generation unit holding frame, a motor 57, an encoder 58, a substrate 59, a motor holding member 60, a cap member 61, and a cam cylinder holding member 62.

The gear head 53, the motor 57, and the encoder 58 are integrally connected with each other in the direction S, and are held by the motor holding member 60 which is fixed to the first casing 51.

With the application of electric power to the motor 57 from the cable 52 via the substrate 59, a gear head shaft 53j of the gear head 53 can be rotated. The cable 52 may be clipped to the universal cord 7.

The gear head shaft 53j is formed with a diameter smaller than the diameter of the gear head 53, the motor 57, and the encoder 58.

The cam cylinder holding member 62 is fixed to the motor holding member 60. The cam cylinder 54 is held by the cam cylinder holding member 62 such that the cam cylinder 54 is non-rotatable in the circumferential direction C, the cam cylinder 54 covering the outer periphery of the gear head shaft 53j, and being coaxial with the gear head shaft 53j in the direction S.

For attaching the power generation unit 50 to the power relay unit 80, the outer periphery of the cam cylinder 54 shown in FIG. 7 has two cam grooves 54m in the circumferential direction C at positions which face each other, the cam protrusions 87p being fitted into the two cam grooves 54m in the circumferential direction C as shown in FIG. 9.

Therefore, the cam cylinder 54 is inserted into or removed from the relay unit holding frame 87 in the direction S, and the cam protrusions 87p are fitted into or detached from the cam grooves 54m with a relative rotation between the relay unit holding frame 87 and the cam cylinder 54 in the circumferential direction C, so that the power generation unit 50 is attached to or detached from the power relay unit 80.

Specifically, in mounting the power generation unit 50 on the power relay unit 80, the cam cylinder 54 is moved toward the one side S1 so as to cause the cam cylinder 54 to be fitted into the relay unit holding frame 87. At this point of operation, the cam protrusions 87p are fitted into fitting ports 54ma of the cam grooves 54m.

Thereafter, when the power generation unit 50 is rotated in the clockwise direction in the circumferential direction C, the cam protrusions 87p move through the cam grooves 54m until the cam protrusions 87p are brought into contact with end portions 54mb of the cam grooves 54m in the circumferential direction C. As a result, the power generation unit 50 is mounted on the power relay unit 80.

In contrast, in detaching the power generation unit 50 from the power relay unit 80, the cam cylinder 54 is rotated with respect to the relay unit holding frame 87 in the counterclockwise direction in the circumferential direction C. With such an operation, the cam protrusions 87p move through the cam grooves 54m to the fitting ports 54ma in a direction opposite to the direction of mounting in the circumferential direction C.

Thereafter, when the power generation unit 50 is moved toward the other side S2, the cam protrusions 87p are removed from the cam grooves 54m, and the cam cylinder 54 is detached from the relay unit holding frame 87 toward the other side S2, so that the power generation unit 50 is detached from the power relay unit 80.

The attachment or detachment of the power generation unit 50 to or from the power relay unit 80 may be performed such that, in contrast to the above, cam protrusions provided to the outer periphery of the cam cylinder 54 are fitted into or detached from cam grooves formed in the relay unit holding frame 87.

The cap member 61 is fixed to the outer periphery of the end portion of the gear head shaft 53j on the one side S1 in the direction S in a state of covering the outer periphery of the end portion, the cap member 61 having a substantially angled-U shape in cross section.

As shown in FIG. 7, the cap member 61 has a cross-shaped protruding portion 61t on the end surface of the gear head shaft 53j on the one side S1. The cross-shaped protruding portion 61t has a cross shape as viewed in a plan view, and has four tapered surfaces tapering toward the one side S1.

The cross shape as viewed in a plan view of the protruding portion 61t merely forms an example, and the protruding portion 61t may have any shape except for a true circle provided that the shape of the protruding portion 61t is the same as the shape of the recessed portion 92p. In other words, the protruding portion 61t may have any shape provided that the shape allows the protruding portion 61t to be fitted with the recessed portion 92p in the circumferential direction C.

In the above-mentioned embodiment, the description has been made by taking the case where the cap member 61 has the cross-shaped protruding portion 61t and the cap member 92 has the cross-shaped recessed portion 92p, as an example. However, the configuration is not limited to the above. Provided that the cap member 61 and the cap member 92 can be fitted with each other, the cap member 61 may have a cross-shaped recessed portion, and the cap member 92 may have a cross-shaped protruding portion.

Further, the outer periphery of the cap member 61 is covered by the cam cylinder holding member 62 via an O-ring 55, and the cam cylinder 54 floats from a portion of the cam cylinder holding member 62 via an elastic member 63.

With the elastic member 63, the cam cylinder 54 floats from the cam cylinder holding member 62, the motor holding member 60, and the first casing 51.

Assume the case where, in mounting the power generation unit 50 on the power relay unit 80, the cam cylinder 54 is fitted into the relay unit holding frame 87 toward the one side S1 in the direction S, and the cam protrusions 87p are fitted into the cam grooves 54m with the relative rotation between the relay unit holding frame 87 and the cam cylinder 54 in the circumferential direction C. In such a case, the gear head shaft 53j is coaxial with the relay unit rotation shaft 83j and hence, the cross-shaped protruding portion 61t is fitted with the cross-shaped recessed portion 92p.

The cross-shaped protruding portion 61t has the four tapered surfaces tapered toward the one side S1. The reason is as follows. In causing the cross-shaped protruding portion 61t to be fitted with the cross-shaped recessed portion 92p, the axis of the cross-shaped protruding portion 61t is caused to approach the axis of the cross-shaped recessed portion 92p to improve fitting accuracy.

The cross-shaped protruding portion 61t is tightly fitted with the cross-shaped recessed portion 92p after the gear head shaft 53j is rotated. The reason is as follows. With the rotation of the cross-shaped protruding portion 61t with respect to the cross-shaped recessed portion 92p in the circumferential direction C, recesses and protrusions are brought into contact with each other in the circumferential direction C and hence, a gap in the circumferential direction C is eliminated.

The cross-shaped protruding portion 61t is fitted with the cross-shaped recessed portion 92p as follows. As shown in FIG. 8 and FIG. 9, when the power generation unit 50 is mounted on the power relay unit 80, specifically, when the cam cylinder 54 is fitted into the relay unit holding frame 87 toward the one side S1 in the direction S, the gear head shaft 53j pushes the cap member 92 and the relay unit rotation shaft 83j toward the one side S1 via the cap member 61, so that the ball 88 pushes the elastic member 82 toward the one side S1. At such a point of operation, the reaction force of the elastic member 82 is generated toward the other side S2. Due to such reaction force, the cross-shaped recessed portion 92p is urged toward the other side S2 against the cross-shaped protruding portion 61t via the relay unit rotation shaft 83j and the cap member 92.

In other words, the elastic member 82 absorbs the displacement of the relay unit rotation shaft 83j until the cross-shaped protruding portion 61t is properly fitted with the cross-shaped recessed portion 92p in the direction S.

As a result, when the gear head shaft 53j is rotated, due to the fitting of the cross-shaped protruding portion 61t with the cross-shaped recessed portion 92p, the rotational force of the gear head shaft 53j is transmitted to the relay unit rotation shaft 83j via the cap members 61, 92.

Therefore, the spur gear 83 rotates and hence, the rotational force is transmitted to the shaft 85j via the idler gear 84 and the spur gear 85, and is transmitted to the pulley 42 via the bevel gears 86, 41 and the shaft 41j.

In other words, the power generation unit 50 transmits a driving force for bending the second bending portion 4b in at least one direction to the second bending portion 4b via the long member 43 wound around the pulley 42.

Note that the other configurations of the endoscope 1 are well-known and hence, the description of the other configurations will be omitted.

As described above, in the present embodiment, it is described that the power generation unit 50, which generates a driving force for bending the second bending portion 4b, is disposed in the operation element area 6c on the second side J2 in the direction J, and is disposed along the universal cord 7 in the direction S.

With such a configuration, when the operator grasps the operation portion 6 with the left hand L as shown in FIG. 2, the power generation unit 50 is provided in the operation element area 6c on the second side J2 in the direction J and hence, the center of gravity of the power generation unit 50 is close to the operation element area 6c whereby excellent weight balance can be acquired.

Further, the direction S in which the action generation unit 50 is arranged differs from the longitudinal direction N and hence, the center of gravity of the power generation unit 50 approaches the operation element area 6c whereby weight balance is improved.

The power generation unit 50 is not provided at a position close to the knobs 11, 12 in the direction J and hence, there is no possibility of the loss of operability of the knobs 11 to 13 and the levers 14, 40 by the thumb LO which sandwiches the bend preventing portion 7k with the forefinger LH. Therefore, desirable accessibility can be ensured.

The power generation unit 50 is provided on the second side J2 and hence, in performing the switching operation of any one of various switch buttons 31 to 33, 35 to 37 with the forefinger LH of the left hand L of the operator, there is no possibility that the power generation unit 50 becomes an obstacle. In other words, accessibility of the forefinger H to the various switch buttons 31 to 33, 35 to 37 is improved compared with the conventional technique.

In the above-mentioned embodiment, it is described that the power generation unit 50 is attached to the operation portion 6, that is, to the power relay unit 80 in the direction S, the power generation unit 50 transmitting power to the power transmission unit 40, and being disposed along the universal cord 7.

It is also described that the mechanism which transmits power of the power generation unit 50 to the power transmission unit 40 is not provided to the power generation unit 50, but is integrated into the power transmission unit 40 and the power relay unit 80.

With such a configuration, it is possible to reduce the number of parts of the power generation unit 50, and the power transmitting mechanism can be integrated into the endoscope 1, that is, into the operation portion 6. Therefore, even if a failure occurs in the power generation unit 50, it is sufficient to remove the power generation unit 50 from the power relay unit 80 for replacement and hence, repairability is improved.

Different from the conventional technique, it is unnecessary to mount wheels to the knobs 11, 12 so as to transmit power of the power generation unit 50 to the power transmission unit 40. Therefore, it is possible to reduce the size of the power transmitting mechanism by a corresponding amount.

Further, there is no possibility that the operation portion 6 has an extremely large weight on the first side J1 in the direction J due to the power generation unit 50 mounted on the knobs 11, 12, thus deteriorating weight balance.

The configuration which uses the power relay unit 80 is adopted, that is, power is not directly transmitted to the power transmission unit 40 from the power generation unit 50. Therefore, it is possible to easily ensure accuracy in relative positions (angles, axial runout) of the respective gears with respect to the pulley 42. Further, it is possible to provide a quiet power transmission configuration where it is possible to prevent variations in tooth contact of respective meshing gears, and teeth are not easily worn.

In the above-mentioned embodiment, it is described that the cam cylinder 54 is inserted into or removed from the relay unit holding frame 87 in the direction S, and the cam protrusions 87p are fitted into or detached from the cam grooves 54m with the relative rotation between the relay unit holding frame 87 and the cam cylinder 54 in the circumferential direction C, so that the power generation unit 50 is attached to or detached from the power relay unit 80.

With such a configuration, for the operation of attaching or detaching the power generation unit 50 to or from the power relay unit 80, only two operations, that is, the movement of the power generation unit 50 in the direction S and the rotation of the power generation unit 50 in the circumferential direction C, are required and hence, the power generation unit 50 can be easily attached to or detached from the power relay unit 80.

Further, two operations are required instead of one operation for attachment or detachment. Therefore, the power generation unit 50 is not easily detached unintentionally. Attachment and detachment of the power generation unit 50 can be achieved with a simple configuration and hence, it is possible to prevent an increase in a diameter of attachment/detachment portions.

In the above-mentioned embodiment, it is described that, when the power generation unit 50 is mounted on the power relay unit 80, the cam protrusions 87p are fitted into the cam grooves 54m, so that the gear head shaft 53j is coaxial with the relay unit rotation shaft 83j.

It is also described that the cross-shaped protruding portion 61t is fitted with the cross-shaped recessed portion 92p and hence, the rotational force of the gear head shaft 53j is transmitted to the relay unit rotation shaft 83j.

It is also described that the relay unit rotation shaft 83j is pushed toward the other side S2 by the elastic member 82 and hence, the cross-shaped protruding portion 61t is fitted with the cross-shaped recessed portion 92p with certainty.

With such a configuration, when the power generation unit 50 is mounted on the power relay unit 80, by merely causing the cam protrusions 87p to be fitted into the cam grooves 54m, the relay unit rotation shaft 83j and the gear head shaft 53j can be easily aligned with high accuracy even without using other tools.

Further, due to a pushing force generated by the elastic member 82, it is possible to eliminate attachment backlash between the cross-shaped protruding portion 61t and the cross-shaped recessed portion 92p.

Therefore, when the gear head shaft 53j is rotated, it is possible to immediately cause the cross-shaped protruding portion 61t to be tightly fitted with the cross-shaped recessed portion 92p and hence, the rotational force of the gear head shaft 53j can be transmitted to the relay unit rotation shaft 83j with certainty without loss.

In addition to the above, also after the cross-shaped protruding portion 61t is fitted with the cross-shaped recessed portion 92p, it is possible to ensure prevention of loosening of fitting between the cross-shaped protruding portion 61t and the cross-shaped recessed portion 92p due to vibrations of the universal cord 7 or the like.

As has been described above, it is possible to provide the endoscope 1 having the configuration where the power generation unit 50 is attached to the operation portion 6 such that the power generation unit 50 can apply power to the power transmission unit 40 with certainty, the power generation unit 50 being attached at a position which can achieve an optimum weight balance, and the power transmitting mechanism is reduced in size.

Second Embodiment

Figure 10:
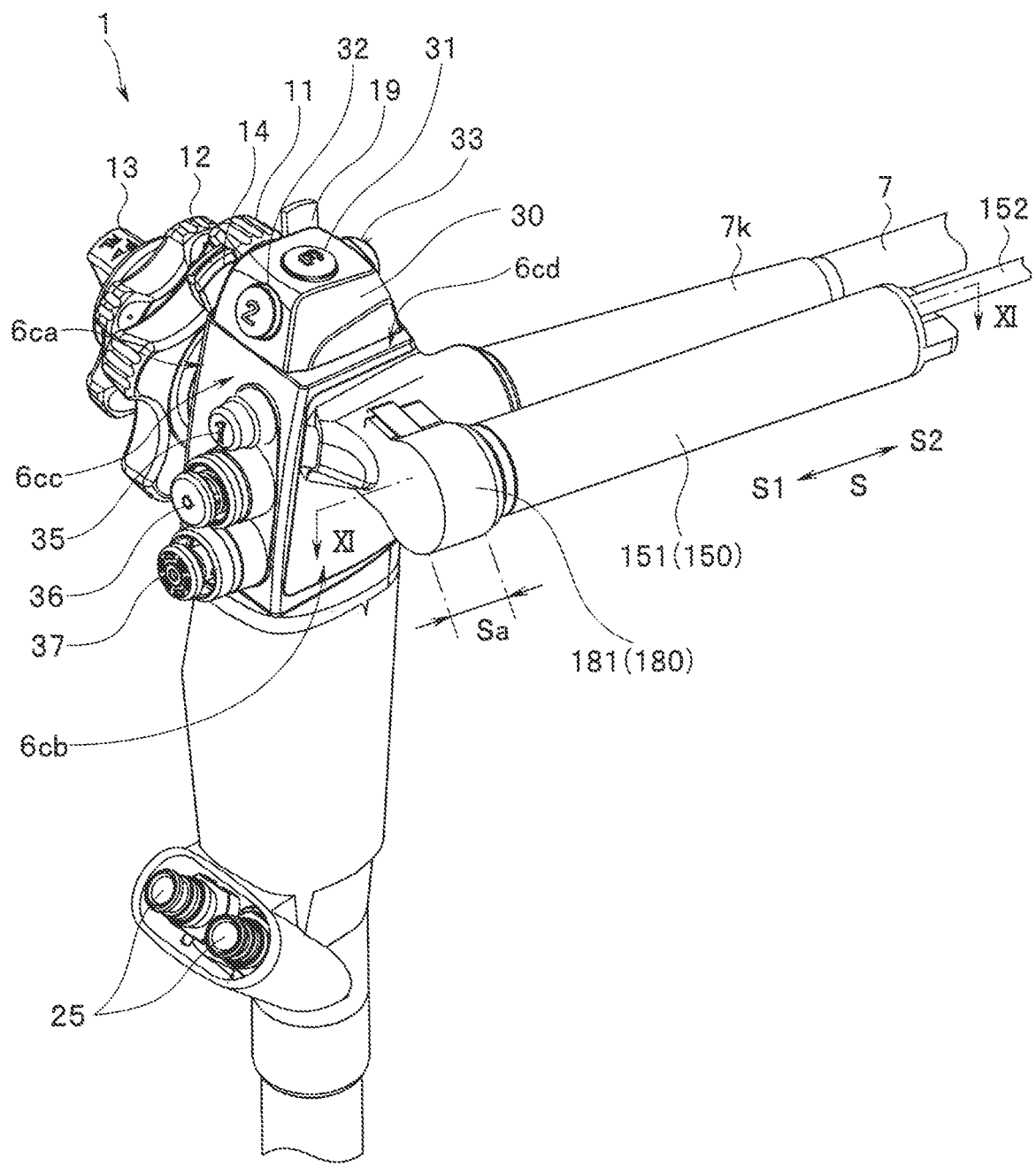
FIG. 10 is a partial perspective view showing an endoscope of a second embodiment.
Figure 11:
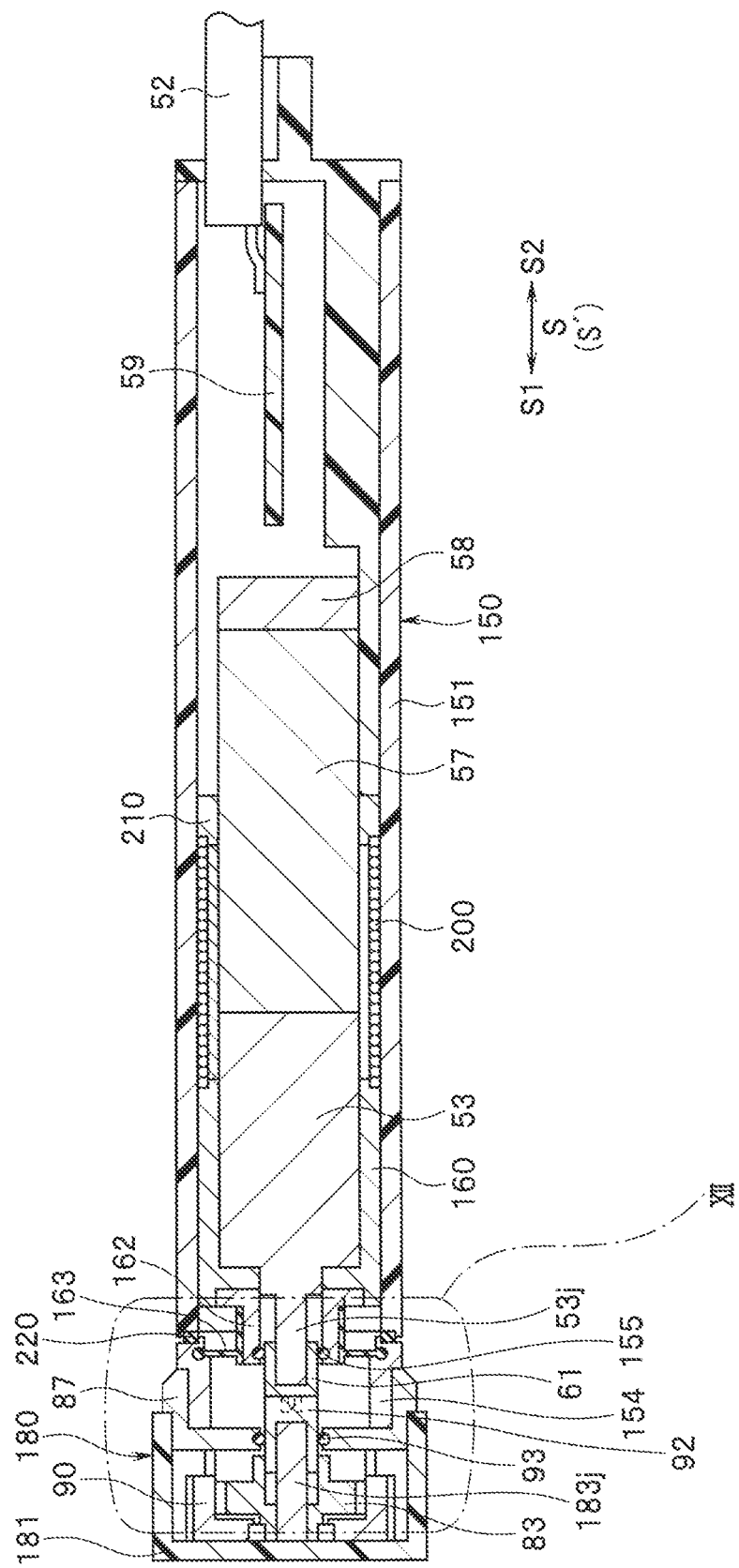
FIG. 11 is a cross-sectional view of a power relay unit and a power generation unit taken along line XI-XI in FIG. 10.
Figure 12:
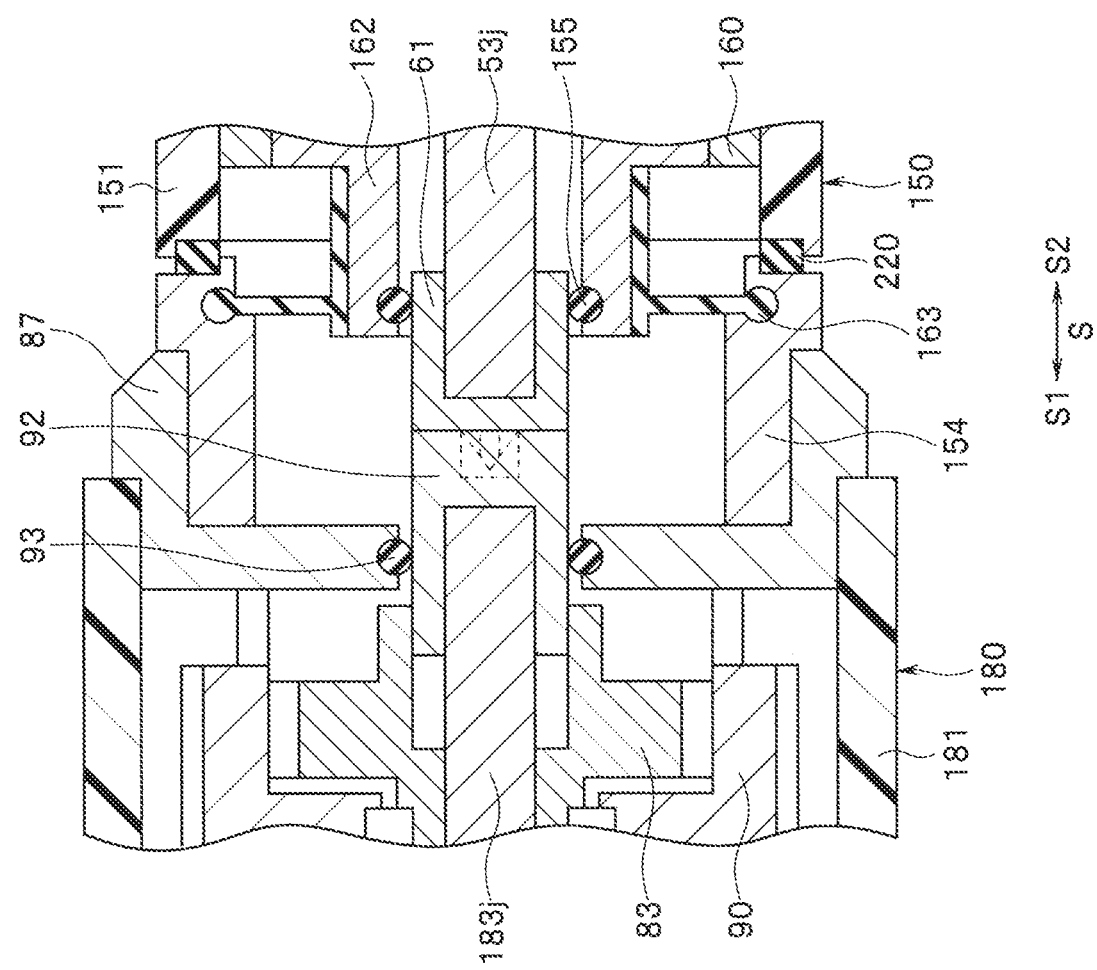
FIG. 12 is a cross-sectional view showing a portion surrounded by a line XII in FIG. 11 in an enlarged manner.
Figure 13:
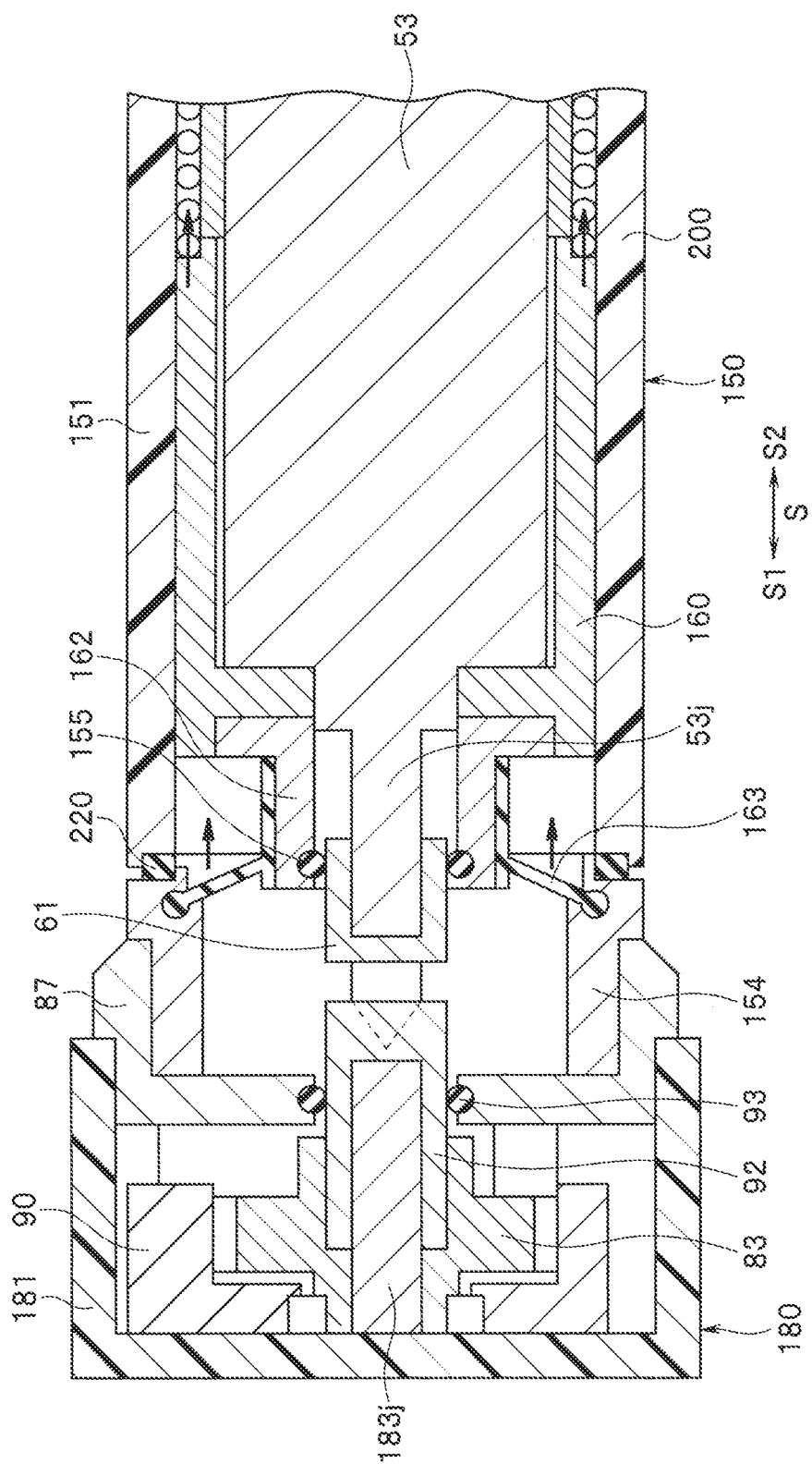
FIG. 13 is a cross-sectional view showing a state where an elastic member of the power generation unit is pushed when the power generation unit is mounted on the power relay unit shown in FIG. 12.

FIG. 10 is a partial perspective view showing an endoscope of the present embodiment. FIG. 11 is a cross-sectional view of a power relay unit and a power generation unit taken along line XI-XI in FIG. 10. FIG. 12 is a cross-sectional view showing a portion surrounded by a line XII in FIG. 11 in an enlarged manner FIG. 13 is a cross-sectional view showing a state where an elastic member of the power generation unit is pushed when the power generation unit is mounted on the power relay unit shown in FIG. 12.

The configuration of the endoscope of the second embodiment differs from the above-mentioned configuration of the endoscope of the first embodiment shown in FIG. 1 to FIG. 9 with respect to a point that the elastic member is provided in the power generation unit.

Therefore, only a point which makes the second embodiment different from the first embodiment will be described. Components identical to the corresponding components in the first embodiment are given the same reference symbols, and the repeated description of such components will be omitted.

As shown in FIG. 10, a power relay unit 180, forming a portion of the operation portion 6, is provided on an opposite side of the first side J1 in the direction J with respect to the operation element area 6c such that the power relay unit 180 protrudes toward the second side J2 from a position where the bend preventing portion 7k of the universal cord 7 is fixed to the surface 6cb of the operation element area 6c of the operation portion 6.

To allow transmission of power, a power generation unit 150 is attached adjacent to the power relay unit 180. The power generation unit 150 may have a structure where the power generation unit 150 is detachable from and attachable to the power relay unit 180 via a cam mechanism or the like, which will be described later. When the power generation unit 150 is mounted on the power relay unit 180, as shown in FIG. 10, the power generation unit 150 is disposed to extend in the direction S.

The power relay unit 180 is connected to the power transmission unit 40 to transmit a rotational force, being power, to the power transmission unit 40.

Specifically, the main part of the power relay unit 180 is formed such that a second casing 181 houses the spur gear 83, the idler gear 84, the shaft 84j which pivotally supports the idler gear 84, the bevel gear 86, the spur gear 85, the shaft 85j which pivotally supports the bevel gear 86 and the spur gear 85, the relay unit holding frame 87, a relay unit rotation shaft 183j which pivotally supports the spur gear 83, and the gear box 90.

The spur gear 83 is pivotally supported on the relay unit rotation shaft 183j such that the spur gear 83 can be rotated, the relay unit rotation shaft 183j being positioned to extend in the second power transmission shaft direction S' which is substantially parallel to the direction S, and which is non-parallel to the first power transmission shaft direction N'.

The spur gear 83 transmits the rotational force transmitted from the relay unit rotation shaft 183j to the idler gear 84.

In other words, when the relay unit rotation shaft 183j is rotated, the spur gear 83 rotates and hence, the rotational force is transmitted to the idler gear 84, the spur gear 85, and the shaft 85j in the direction J whereby the bevel gear 86 is rotated.

Thereafter, the bevel gear 41 which is meshed with the bevel gear 86 is rotated and hence, the rotation direction is changed, and the shaft 41j is rotated, so that the pulley 42 is rotated.

As a result, either one of the two long members 43 is pulled due to the rotation, so that the second bending portion 4b is bent in either one of two directions in the present embodiment.

The above-mentioned cap member 92 is fixed to the outer periphery of the end portion of the relay unit rotation shaft 183j on the other side S2 in the direction S in a state of covering the outer periphery of the end portion.

The outer periphery of the cap member 92 is covered by the relay unit holding frame 87 via the O-ring 93 such that the relay unit holding frame 87 is coaxial with the relay unit rotation shaft 183j in the direction S.

The relay unit holding frame 87 is fixed to the inner peripheral surface of the second casing 181. Therefore, there is no possibility that the relay unit holding frame 87 rotates in the circumferential direction C with the rotation of the relay unit rotation shaft 183j.

The relay unit rotation shaft 183j and the cap member 92 can be, with respect to the relay unit holding frame 87, not only rotated in the circumferential direction C but also moved toward the one side S1 and the other side S2 in the direction S in a state of being in contact with the O-ring 93.

Further, when the power generation unit 150 is mounted on the power relay unit 180, a cam cylinder 154, which will be described later, is fitted into the relay unit holding frame 87 in the direction S as shown in FIG. 11 to FIG. 13.

The power generation unit 150 applies power to the power relay unit 180 in the direction S. Specifically, the main part of the power generation unit 150 is formed such that a first casing 151 houses the end portion of the cable 52, the gear head 53, the motor 57, the encoder 58, the substrate 59, the cap member 61, the cam cylinder 154, being the generation unit holding frame, a motor holding member 160, a cam cylinder holding member 162, a film-like watertight member 163, an elastic member 200, a spring holding member 210, and an elastic member 220.

The gear head 53, the motor 57, and the encoder 58 are integrally connected with each other in the direction S, and are held by the motor holding member 160 which is fixed to the first casing 151.

The cam cylinder holding member 162 is fixed to the motor holding member 160. The cam cylinder 154 is held by the cam cylinder holding member 162 such that the cam cylinder 154 is non-rotatable in the circumferential direction C, the cam cylinder 154 covering the outer periphery of the gear head shaft 53j, and being coaxial with the gear head shaft 53j in the direction S.

Further, the film-like watertight member 163 is provided to the inner peripheral surface of the cam cylinder 154 circumferentially in the circumferential direction C, the film-like watertight member 163 being brought into contact with the outer peripheral surface of the cam cylinder holding member 162.

When the power generation unit 150 is mounted on the power relay unit 180, as shown in FIG. 13, the cam cylinder holding member 162 may be pushed toward the other side S2 by the cam cylinder 154, thus moving toward the other side S2. Even in such a case, the watertight member 163 is deformed toward the other side S2 following the movement of the cam cylinder holding member 162 to maintain watertightness in the first casing 151 from the cam cylinder 154 side. With such a configuration, durability of the power generation unit 150 is improved.

Further, the elastic member 220 is provided between the cam cylinder 154 and the first casing 151 in the direction S, the elastic member 220 causing the first casing 151 to float from the cam cylinder 154 in the direction S.

In the first casing 151, the elastic member 200 is positioned to extend in the direction S between the motor holding member 160 and the spring holding member 210 in the direction S, the spring holding member 210 being fixed to the first casing 151.

The elastic member 200 is formed of a coil spring, for example. With the urging of the motor holding member 160 toward the one side S1 in the direction S, the elastic member 200 causes the power generation unit 50 to be brought into close connect with the power relay unit 80 to apply the rotational force of the power generation unit 50 to the power relay unit 80 with certainty.

Although not shown in the drawing, also in the present embodiment, the outer periphery of the cam cylinder 154 has two cam grooves in the circumferential direction C at positions which face each other, the cam protrusions 87p being fitted into the cam grooves in the circumferential direction C when the power generation unit 150 is mounted on the power relay unit 180.

Therefore, the cam cylinder 154 is inserted into or removed from the relay unit holding frame 87 in the direction S, and the cam protrusions 87p are fitted into or detached from the cam grooves with the relative rotation between the relay unit holding frame 87 and the cam cylinder 154 in the circumferential direction C, so that the power generation unit 150 is attached to or detached from the power relay unit 180.

The specific configuration of attaching or detaching the power generation unit 150 to or from the power relay unit 180 by using the cam grooves and the cam protrusions 87p and the specific configuration of causing the cross-shaped protruding portion 61t to be fitted with the cross-shaped recessed portion 92p at the time of mounting the power generation unit 150 on the power relay unit 180 are substantially equal to the corresponding configurations in the above-mentioned first embodiment and hence, the repeated description of such configurations will be omitted.

However, in the present embodiment, the cross-shaped protruding portion 61t is fitted with the cross-shaped recessed portion 92p as follows. As shown in FIG. 12, when the power generation unit 150 is mounted on the power relay unit 180, specifically, when the cam cylinder 154 is fitted into the relay unit holding frame 87 toward the one side S1 in the direction S, the cam cylinder 154, the cam cylinder holding member 162, which holds the cam cylinder 154, and the motor holding member 160 push the elastic member 200 against the spring holding member 210 toward the other side S2 together with the gear head 53, the motor 57, and the encoder 58.

Thereafter, due to the reaction force of the elastic member 200, the gear head 53, the motor 57, and the encoder 58 are pushed against the relay unit holding frame 87 toward the one side S1 together with the cam cylinder 154 via the motor holding member 160 and the cam cylinder holding member 162.

As a result, the cross-shaped protruding portion 61*t* is urged toward the one side S1 against the cross-shaped recessed portion 92*p*, thus being tightly fitted and connected with the cross-shaped recessed portion 92*p*.

In other words, the elastic member 200 absorbs the displacement of the cam cylinder 154 until the cross-shaped protruding portion 61*t* is properly fitted with the cross-shaped recessed portion 92*p* in the direction S.

As a result, when the gear head shaft 53*j* is rotated, due to the fitting of the cross-shaped protruding portion 61*t* with the cross-shaped recessed portion 92*p*, the rotational force of the gear head shaft 53*j* is transmitted to the relay unit rotation shaft 183*j* via the cap members 61, 92.

Therefore, the spur gear 83 rotates and hence, the rotational force is transmitted to the shaft 85*j* via the idler gear 84 and the spur gear 85, and is transmitted to the pulley 42 via the bevel gears 86, 41, and the shaft 41*j*.

In other words, the power generation unit 150 transmits a driving force for bending the second bending portion 4*b* in at least one direction to the second bending portion 4*b* via the long member 43 wound around the pulley 42.

Note that the other configurations of the endoscope 1 are substantially equal to the corresponding configurations in the above-mentioned first embodiment.

As described above, in the present embodiment, it is described that the elastic member 200 is provided in the power generation unit 150. When the power generation unit 150 is mounted on the power relay unit 180, the elastic member 200 urges the power generation unit 150 against the power relay unit 180 to cause the cross-shaped protruding portion 61*t* to be tightly fitted with the cross-shaped recessed portion 92*p*.

With such a configuration, it is unnecessary to provide an elastic member in the power relay unit 180 and hence, as shown in FIG. 1 and FIG. 10, the length of the power relay unit 180 in the direction S can be shortened (Sa<Sb). Therefore, ease of the operator grasping the grasping area 6*c* is further improved.

Other advantageous effects are substantially equal to the advantageous effects of the above-mentioned first embodiment.

In the above-mentioned first and second embodiments, it is described that the power generation unit 50, 150 transmits a driving force for bending the second bending portion 4*b* via the power relay unit 80, 180 and the power transmission unit 40.

However, the configuration is not limited to the above. For example, needless to say, such a configuration is also applicable to a configuration of transmitting a driving force for bending the first bending portion 4*a* with the operation of the knobs 11, 12.

Further, needless to say, even when such a configuration is used for a configuration of transmitting a driving force for electrically driving another specific portion provided to the insertion portion 2 other than the second bending portion 4*b*, for example, a rotating body provided to the distal end portion 3, it is possible to obtain advantageous effects substantially equal to the advantageous effects of the present embodiment.

What is claimed is:

1. An endoscope comprising:
    an insertion portion configured to be inserted into an object or a subject;
    an operation portion provided on a proximal end side of the insertion portion in a longitudinal direction in which the insertion portion extends, the operation portion being grasped by an operator, and being configured to perform an operation of the insertion portion;
    a power transmitting mechanism provided in the operation portion, and configured to transmit power to a specific portion of the insertion portion;
    a power relay mechanism connected to the power transmitting mechanism, and configured to transmit the power to the power transmitting mechanism;
    a power generation device attached adjacent to the power relay mechanism, and configured to apply the power to the power relay mechanism in a second power transmission shaft direction which is non-parallel to a first power transmission shaft direction of the power transmitting mechanism;
    an elastic member configured to perform either one of urging the power relay mechanism against the power generation device or urging the power generation device against the power relay mechanism; and
    a cable configured to extend from the operation portion in the second power transmission shaft direction which is a direction different from the longitudinal direction, wherein
    the power generation device is attached such that the power generation device is disposed to extend in an extending direction of the cable after being mounted.

2. The endoscope according to claim 1, wherein
    the power applied to the power relay mechanism from the power generation device is a rotational force, and
    with the urging, the elastic member causes one of the power generation device or the power relay mechanism to be brought into close contact with another of the power generation device or the power relay mechanism to apply the rotational force of the power generation device to the power relay mechanism.

3. The endoscope according to claim 2, wherein
    the power relay mechanism includes one of a cam groove or a cam protrusion, and the power generation device includes another of the cam groove or the cam protrusion, the cam groove and the cam protrusion engaging with each other.

4. The endoscope according to claim 3, wherein
    the power relay mechanism includes a relay unit rotation shaft, and a relay unit holding frame which covers an outer periphery of the relay unit rotation shaft, the relay unit holding frame being coaxial with the relay unit rotation shaft in the second power transmission shaft direction, and being non-rotatable,
    the power generation device includes a generation unit rotation shaft, and a generation unit holding frame which covers an outer periphery of the generation unit rotation shaft, the generation unit holding frame being coaxial with the generation unit rotation shaft in the second power transmission shaft direction, and being non-rotatable, the relay unit holding frame has the one of the cam groove or the cam protrusion, and the generation unit holding frame has the other of the cam groove or the cam protrusion, and in a state where the cam protrusion is fitted into the cam groove, the relay unit holding frame independently rotates relative to the relay unit rotation shaft, and the generation unit holding frame independently rotates relative to the generation unit rotation shaft.

5. The endoscope according to claim 4, wherein
the relay unit rotation shaft has one of a recess or a protrusion at a portion where the relay unit rotation shaft is connected with the generation unit rotation shaft, and the generation unit rotation shaft has another of the recess or the protrusion at a portion where the generation unit rotation shaft is connected with the relay unit rotation shaft, the recess and the protrusion are fitted with each other with urging of the elastic member.

6. The endoscope according to claim 1, wherein
in the second power transmission shaft direction, the elastic member performs either one of urging the power relay mechanism against the power generation device or urging the power generation device against the power relay mechanism.

7. The endoscope according to claim 1, wherein
the elastic member is attached in a first casing or a second casing, the first casing supporting the power generation device, the second casing supporting the power relay mechanism.

8. The endoscope according to claim 1, wherein
the operation portion is provided with a knob which protrudes from the operation portion in a direction intersecting with the longitudinal direction, the knob being configured to perform an operation of the specific portion or another specific portion of the insertion portion, and the power relay mechanism is positioned on an opposite side of the knob with respect to the operation portion in the direction intersecting with the longitudinal direction.

9. The endoscope according to claim 8, wherein
the knob performs the operation of the other specific portion, and an action of the other specific portion performed with the operation of the knob differs from an action of the specific portion performed with transmission of the power from the power generation device via the power relay mechanism and the power transmitting mechanism.

10. The endoscope according to claim 9, wherein
the other specific portion of the insertion portion is a first bending portion provided on a distal end side of the insertion portion in the longitudinal direction, the first bending portion being configured to perform a bending action in a plurality of directions corresponding to the operation of the knob, the specific portion of the insertion portion is a second bending portion continuously formed with a proximal end of the first bending portion in the longitudinal direction, and the power generation device transmits a driving force for bending the second bending portion in at least one direction to the second bending portion from the operation portion via a long member of the power transmitting mechanism.

11. The endoscope according to claim 1, wherein
the power generation device has a structure which is detachable from and attachable to the power relay mechanism.

* * * * *